(12) United States Patent
Zhu et al.

(10) Patent No.: US 9,538,760 B2
(45) Date of Patent: *Jan. 10, 2017

(54) DISINFECTANT COMPOSITIONS WITH HYDROGEN PEROXIDE

(71) Applicant: Arkema Inc., King of Prussia, PA (US)

(72) Inventors: Shui-Ping Zhu, Gurnee, IL (US); Stephen W. Carson, Coatesville, PA (US); Xue Wang, Sugar Land, TX (US)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/544,607

(22) Filed: Jan. 26, 2015

(65) Prior Publication Data

US 2015/0150263 A1  Jun. 4, 2015

Related U.S. Application Data

(62) Division of application No. 13/253,253, filed on Oct. 5, 2011, now abandoned.

(51) Int. Cl.
*A01N 59/00* (2006.01)

(52) U.S. Cl.
CPC .................................... *A01N 59/00* (2013.01)

(58) Field of Classification Search
None
See application file for complete search history.

(56) References Cited

U.S. PATENT DOCUMENTS

| | | | |
|---|---|---|---|
| 5,827,542 A | 10/1998 | Minor et al. | |
| 5,891,392 A | 4/1999 | Monticello et al. | |
| 6,106,854 A * | 8/2000 | Belfer | A01N 59/00 424/405 |
| 6,479,454 B1 | 11/2002 | Smith et al. | |
| 6,627,589 B1 | 9/2003 | Arvanitidou | |
| 6,841,090 B1 * | 1/2005 | Serego Allighieri | A01N 25/02 252/186.1 |
| 6,908,628 B2 | 6/2005 | Herruzo Cabrera | |
| 2002/0142051 A1 | 10/2002 | Rochon | |
| 2003/0031687 A1 | 2/2003 | Falder et al. | |
| 2003/0180377 A1 | 9/2003 | Ramirez et al. | |
| 2005/0019421 A1 | 1/2005 | Hobbs et al. | |
| 2005/0058719 A1 | 3/2005 | Ramirez et al. | |
| 2005/0148485 A1 | 7/2005 | Cheung et al. | |
| 2005/0255172 A1 | 11/2005 | Omidbakhsh | |
| 2006/0100122 A1 | 5/2006 | Baars et al. | |
| 2006/0193816 A1 | 8/2006 | Elfersv et al. | |
| 2007/0166337 A1 * | 7/2007 | Treudler | A61K 8/0208 424/401 |
| 2007/0166398 A1 | 7/2007 | Bobbert | |
| 2009/0304608 A1 * | 12/2009 | Cueman | A61K 8/22 424/53 |
| 2010/0055198 A1 | 3/2010 | Wang et al. | |
| 2010/0331227 A1 | 12/2010 | Papari et al. | |

FOREIGN PATENT DOCUMENTS

| | | |
|---|---|---|
| WO | WO 97/31889 | 9/1997 |
| WO | WO 03/076560 A1 | 9/2003 |
| WO | WO 2008/071746 A1 | 6/2008 |

* cited by examiner

*Primary Examiner* — Jianfeng Song
(74) *Attorney, Agent, or Firm* — Steven D. Boyd

(57) ABSTRACT

Disinfectant compositions include 0.001 to 10% by weight of hydrogen peroxide or a hydrogen peroxide source based on the total weight of the composition; 0.001 to 20% by weight of at least one amphoteric surfactant based on the total weight of the composition; and 0.001 to 0.8% by weight of at least one alkali metal or alkaline earth metal salt of a cyclic or heterocyclic aromatic compound comprising at least one hydroxyl group, carboxylic group, or combination thereof based on the total weight of the composition. The disinfectant compositions are particularly effective at treating surfaces contaminated with resistant bacteria, such as *Staphylococcus aureus* at a fast killing rate.

17 Claims, No Drawings

DISINFECTANT COMPOSITIONS WITH HYDROGEN PEROXIDE

This application is a divisional application of, and claims priority to, U.S. application for patent Ser. No. 13/253,253 filed Oct. 5, 2011, which application is incorporated by reference into this application

FIELD OF THE INVENTION

The invention relates to disinfectant compositions comprising hydrogen peroxide and methods of disinfecting surfaces using such compositions.

BACKGROUND OF THE INVENTION

Hydrogen peroxide ($H_2O_2$) is generally considered an acceptable "green" bleaching agent from a toxicological and environmental standpoint because its decomposition and biodegradation products are oxygen and water. Hydrogen peroxide is used in household laundry bleach, disinfectants, hard surface cleansers, and other cleaning compositions because hydrogen peroxide compositions are usually fiber-safe and color-safe.

Although disinfectant compositions containing hydrogen peroxide are widely known throughout the industry and in the prior art, some strains of microbes, bacteria, viruses, etc. are especially resistant to hydrogen peroxide compositions, even though the compositions may contain a high amount of hydrogen peroxide. Moreover, known hydrogen peroxide disinfectant compositions or sanitizers may have an effective "killing power" but at a very slow rate, e.g., on the order of hours. Thus, a hydrogen peroxide composition is desired that could disinfect a wide spectrum of germs and viruses (even especially virulent or resistant ones), with a high killing power, in a short period of time.

SUMMARY OF THE INVENTION

The present invention provides for such disinfectant compositions comprising hydrogen peroxide, which exhibit a high killing power (e.g., ≥99.999%) at a fast killing rate (e.g., 30 seconds or less) with wide spectrum biocidal activity and effects (e.g., killing bacteria, fungi, spores, viruses, moulds and yeast, etc., including virulent strains such as *Staphylococcus aureus*).

According to an embodiment of the present invention, a disinfectant composition comprises: 0.001 to 10% by weight of hydrogen peroxide or a peroxide source based on the total weight of the composition; 0.001 to 20% by weight of at least one amphoteric surfactant based on the total weight of the composition; and 0.001 to 0.8% by weight of at least one alkali metal or alkaline earth metal salt of a cyclic or heterocyclic aromatic compound comprising at least one hydroxyl group, carboxylic group, or combination thereof based on the total weight of the composition.

According to another embodiment of the present invention, a disinfectant composition comprises: about 2% to about 4% (e.g., about 3%) by weight of hydrogen peroxide or a peroxide source based on the total weight of the composition; about 0.3% to about 0.7% (e.g., about 0.5%) by weight of cocoamidopropyl betaine based on the total weight of the composition; about 0.03% to about 0.07% (e.g., about 0.05%) by weight of sodium salicylate based on the total weight of the composition; and water.

According to another embodiment of the present invention, the disinfectant composition has a pH in the range of 0.1-6, more particularly, an acidic pH in the range of about 3-4 (e.g., about 3.0 to about 3.5).

According to another embodiment of the present invention, a method of disinfecting a surface contaminated with microorganisms includes contacting the surface with a disinfectant composition containing hydrogen peroxide or a peroxide source, an amphoteric surfactant; and an alkali metal or alkaline earth metal salt of a cyclic or heterocyclic aromatic compound comprising at least one hydroxyl group, carboxylic group, or combination thereof. The disinfectant compositions are particularly effective at treating surfaces contaminated with resistant bacteria, such as *Staphylococcus aureus*, at a fast killing rate.

DETAILED DESCRIPTION OF THE INVENTION

Aspects of the present invention include hydrogen peroxide compositions, disinfectant compositions comprising hydrogen peroxide, and methods of disinfecting surfaces using such disinfectant compositions.

As used herein, "disinfectant" or "disinfecting" is meant to encompass compositions having the ability of reducing or eliminating (e.g., killing) the microorganisms (e.g., bacteria, fungi, spores, viruses, moulds and yeast, etc.) existing on a surface. An effective amount of a disinfectant would include an amount sufficient to allow the disinfectant to perform its action, i.e., reduce the number of microorganisms existing on a given surface. The disinfectant compositions may also be termed antimicrobial compositions in that the disinfectant properties may attack the vital function of the microorganisms.

As used herein, killing power and killing rate are used to denote the potency or effectiveness of the disinfectant compositions. A disinfectant composition having a high killing power reduces or eliminates all or substantially all of the microorganisms (e.g., bacteria, fungi, spores, viruses, moulds and yeast, etc.). Thus, a high killing power may be on the order of ≥99%, ≥99.9%, ≥99.99%, or ≥99.999%. A disinfectant composition having a high killing rate reduces or eliminates the microorganisms in a short period of time. Thus, a high killing rate may be on the order of within 10 minutes, within 5 minutes, within 1 minute, within 30 seconds, or within 10 seconds. In other words, at the expiry of a given duration, the number of microorganisms is reduced to the given killing power.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of." Unless specified otherwise, all values provided herein include up to and including the endpoints given, and the values of the constituents or ingredients of the compositions are expressed in weight percent or % by weight of each ingredient in the composition.

According to an aspect of the present invention, the disinfectant composition comprises hydrogen peroxide or a peroxide source, at least one amphoteric surfactant; and at least one alkali metal or alkaline earth metal salt of a cyclic or heterocyclic aromatic compound comprising at least one hydroxyl group, carboxylic group, or combination thereof.

The disinfectant composition comprises hydrogen peroxide or a hydrogen peroxide source. The type and form of hydrogen peroxide or a source thereof used in the disinfectant compositions of the present invention are not particularly limited. Hydrogen peroxide may refer to the compound per se and/or sources or compounds which release hydrogen peroxide in solution, such as sodium peroxide. The hydrogen peroxide may be formed from precursors, such as percarbonates (e.g., sodium percarbonate) under conditions known to those of ordinary skill in the art. Thus, the hydrogen peroxide source can refer to any compound which produces hydrogen peroxide (e.g., when in contact with water). Suitable water-soluble sources of hydrogen peroxide may include, but are not limited to, percarbonates, persilicates, persulphates such as monopersulfate, perborates and peroxyacids such as diperoxydodecandioic acid (DPDA), magnesium perphthalic acid, and mixtures thereof. The hydrogen peroxide may be added in a neat or dilute form. For example, the hydrogen peroxide may be diluted with water (e.g., distilled, deionized, etc.).

The hydrogen peroxide may be present in the disinfectant composition in amounts ranging from about 10% or less by weight. In other words, only a small amount of hydrogen peroxide (or a source thereof) is required to produce an effective and efficient killing rate. For example, hydrogen peroxide may be present in an amount of about 0.001 to 10%, about 0.1-6% by weight, about 1-5% by weight, about 2-4% by weight, or about 3% by weight. The hydrogen peroxide may be particularly suitable and effective because hydrogen peroxide is a strong oxidizer; the oxidizing property may help to reduce bacterial and viral populations by destroying bacterial and viral cell membranes. The hydrogen peroxide may also remove stains from a surface. Additionally, the non-discriminating and non-selective oxidation by hydrogen peroxide may help minimize future resistant bacterial and viral strains from developing. Furthermore, hydrogen peroxide has excellent biodegradability and produces no hazardous byproducts.

Other components, such as stabilizers, may also be present to stabilize the hydrogen peroxide (e.g., improve its chemical and/or physical stability), as would be well recognized by one of ordinary skill in the art. Suitable stabilizers may include stannates, for examples, such as stannic chloride, stannic oxide, stannic bromide, stannic chromate, stannic iodide, stannic sulfide, tin dichloride bis(2,4-pentanedionate), tin phthalocyanine dichloride, tin acetate, and the like. The hydrogen peroxide may also comprise additional stabilizers, such as aromatic chelating agents or aromatic radical scavengers, known to one of ordinary skill in the art.

The disinfectant composition comprises at least one amphoteric surfactant. As is well known to one of ordinary skill in the art, a surfactant consists of a hydrophobic (non-polar) hydrocarbon "tail" and a hydrophilic (polar) "head" group. As used herein, "amphoteric surfactant" is intended to encompass a surfactant that contains a head with two oppositely charged groups (e.g., positive and negative). Thus, amphoteric surfactants may be anionic (negatively charged), cationic (positively charged) or non-ionic (no charge) in solution, depending on the acidity or pH of the water.

In an exemplary embodiment, the amphoteric surfactant belongs to a class of surfactants where the positive ion and the negative ion of the amphoteric surfactant are separated by more than one atom. In other words, the positive ion and negative ion in the hydrophilic (polar) "head" group are not adjacent to one another. In one embodiment of the present invention, the amphoteric surfactant comprises nitrogen as the positive ion and oxygen as the negative ion.

For instance, the amphoteric surfactant may comprise a surfactant having the following general formula:

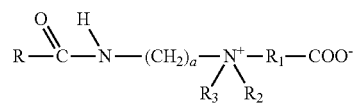

where R, $R_2$, and $R_3$ are each the same or different alkyl groups, $R_1$ is a saturated or unsaturated alkylene group, and $a \geq 1$.

The alkyl groups may be unsubstituted or substituted. An "unsubstituted alkyl" refers to alkyl groups that do not contain heteroatoms, and includes straight chain alkyl groups such as methyl, ethyl, propyl, butyl, pentyl, hexyl, heptyl, octyl, nonyl, decyl, undecyl, dodecyl, and the like; branched chain isomers of straight chain alkyl groups; cyclic alkyl groups, such as cyclopropyl, cyclobutyl, cyclopentyl, cyclohexyl, cycloheptyl, and cyclooctyl and such rings substituted with straight and branched chain alkyl groups as defined above; and may include primary, secondary, or tertiary alkyl groups.

A "substituted alkyl" refers to an unsubstituted alkyl group as defined above in which one or more bonds to carbon(s) or hydrogen(s) are replaced by a bond to non-hydrogen and non-carbon atoms such as, but not limited to, a halogen atom, such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom are replaced by a bond to a heteroatom such as oxygen in groups such as carbonyls, carboxyls, and esters; nitrogen in groups such as imines, oximes, hydrazones, and nitriles. Each of the alkyl groups may have, for example, 1 to 20 carbon atoms, 1 to 10 carbon atoms, 1 to 5 carbon atoms, or 1 to 3 carbon atoms.

The "alkylene" group may be saturated or unsaturated and refers to saturated, divalent straight or branched chain hydrocarbyl groups having in the range of 1 to 20 carbon atoms. The alkylene may also be a "substituted alkylene" in that the alkylene groups further bears one or more substituents as set forth above.

Suitable amphoteric surfactants in accordance with the present invention may include, but are not limited to, betaines, such as amidobetaines, amidosulfobetaines, coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alphacarboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine.

In an exemplary embodiment of the present invention, the amphoteric surfactant comprises one or more amidobetaines. For example, the amphoteric surfactant may comprise a cocoamidopropyl betaine. Preferably, the amphoteric surfactant is a DIE surfactant (i.e., it complies with the Environmental Protection Agency's (EPA) Designed for the Environment (DIE) program). In one embodiment, the amphoteric surfactant is the only type of surfactant present in the disinfectant composition.

Without wishing to be bound to a particular theory, the surfactant may act as a wetting agent to help decrease the surface tension of the liquid, thereby increasing the wettability of the contact surface. Additionally, the surfactant may function to prevent any matter from precipitating out of solution and depositing on surfaces.

The concentration of the amphoteric surfactant may range from about 0.001% to 20%, about 0.01% to 5%, about 0.1% to 1%, about 0.3% to 0.7%, or about 0.5% based on the total weight of the composition.

The disinfectant composition comprises at least one alkali metal or alkaline earth metal salt of a cyclic or heterocyclic aromatic compound comprising at least one hydroxyl group (OH), carboxylic group (COOH), or combination thereof. Without wishing to be bound to a particular theory, it is believed that the salt form is more effective than an acid form. In other words, the selection of a salicylate salt is more desirable than salicylic acid, for example. This may be due, at least in part, because a salt is easier to dissolve in the hydrogen peroxide composition than its equivalent acid form. It will be recognized by one of skill in the art, however, that if a salt is added to the composition but the pH is later brought down to the acidic range, then the salt may also be present in its acid form (e.g., if the pH of a solution equals the pKa, then the acid is in equilibrium, and it is half dissociated).

The disinfectant composition comprises at least one alkali metal or alkaline earth metal salt of a cyclic or heterocyclic aromatic compound. The term "cyclic" is intended to encompass compounds which have at least one ring, such as a benzene ring. A "heterocyclic aromatic compound" pertains to groups or molecules comprising a ring where at least one of the ring atoms is a multivalent ring heteroatom (e.g., nitrogen, oxygen, phosphorous, silicon, or sulfur). The heterocycle may have from 1 to 4 heteroatoms, for example.

In one embodiment of the present invention, the cyclic or heterocyclic aromatic compound is a benzoate, a pyridine, or a salicylate. For example, the benzoate may be of the following formula: $HOC_6H_4COOCH_2CH_3$. In an exemplary embodiment, the benzoate comprises para-hydroxyl ethyl benzoate. The pyridine may be of the following formula: $C_6H_2Cl_3KN_2O_2$. In one embodiment, the pyridine comprises a picolinic acid salt. The salicylate may be of the following formula $X^+C_6H_4(OH)COO^-$, where X is an alkali metal or alkaline earth, such as lithium, sodium, potassium, cesium, magnesium, calcium. For example, the at least one alkali metal salt or alkaline earth metal may be selected from the group consisting of sodium, potassium, magnesium, and calcium. In an exemplary embodiment, the alkali metal or alkaline earth metal is an alkali metal, namely, sodium. Thus, the at least one alkali metal or alkaline earth metal salt of the cyclic or heterocyclic aromatic compound may comprise sodium salicylate.

Preferably, the alkali metal or alkaline earth metal salt of the cyclic or heterocyclic aromatic compound is approved by the Food and Drug Administration (FDA). In one embodiment, the concentration of the at least one alkali metal or alkaline earth metal salt of the cyclic or heterocyclic aromatic compound may range from about 0.001 to 0.8%, about 0.01 to 0.1%, about 0.04 to 0.06%, or about 0.05% by weight based on the total weight of the composition.

In an exemplary embodiment, the hydrogen peroxide composition has an acidic pH up to about 6, e.g., in the range of about 0.1-6, preferably 1-5, more preferably about 2-4, even more preferably an acidic pH in the range of about 3-4 (e.g., about 3.0 to about 3.5 or about 3.2 to about 3.5).

Without wishing to be bound to a particular theory, the selection of an acidic pH for the disinfectant composition may provide certain advantages. In particular, an acidic pH may provide for a more efficient killing rate and killing power. Additionally, the stability of the composition may also be affected by the pH, e.g., a more acidic pH on the order of 3.0 to 3.5, may provide enhanced stability for the disinfectant compositions.

The pH of the disinfectant may be adjusted using a pH adjusting agent, which may include any compound that can affect the pH of the composition, such as acids and bases. The acid(s) and/or base(s) may be added to the composition in any suitable form, such as anhydrous, hydrated, aqueous, salt, etc.

In one embodiment, the pH adjusting agent is a base selected from the group consisting of alkali metal and alkaline earth metal hydroxides, ammonium hydroxide, substituted ammonium hydroxides (such as primary, secondary, tertiary, or quaternary ammonium hydroxides), and mixtures thereof. In an exemplary embodiment, the base is an aqueous sodium hydroxide.

In another embodiment, the pH adjusting agent is an acid. For example, the acid may be a sulfur-containing acid, such as a sulfonic acid (e.g., $R-S(=O)_2-OH$, where R may be hydrogen, aliphatic, cyclic, alicyclic or aromatic and the aliphatic part may be a linear or branched, saturated or unsaturated, substituted or unsubstituted hydrocarbon group), sulfuric acid ($H_2SO_4$), an alkali metal bisulfate, phosphoric acid (or other phosphorous-containings acids), etc. Nitric acid ($HNO_3$) may also be used.

The disinfectant composition may optionally include other ingredients typical in disinfectant compositions. For example, the compositions may comprise one or more additives selected from the group consisting of anionic surfactants, cationic surfactants, nonionic surfactants, bleaching agents, enzymes, fluorescent dyes, color dyes, fragrances, thickening agents, inorganic builders, anti-redeposition agents, corrosion inhibitors, opacifiers, and mixtures thereof.

The disinfectant composition may comprise a surfactant or a mixture of surfactants in addition to the at least one amphoteric surfactant described herein. Numerous surfactants useful in disinfectant compositions are well known to those skilled in the art. The surfactant may be anionic (negative charge), cationic (positive charge), nonionic (no charge), or a mixture thereof. Examples of anionic surfactants include sulfates and sulfates of ethoxylates, sodium cetyl sulfate, sodium lauryl sulfate, sodium myristyl sulfate, sodium stearyl sulfate, sodium dodecylbenzene sulfonate, and sodium polyoxyethylene lauryl ether sulfate. Examples of cationic surfactants may include didecyl dimethyl ammonium chloride, octyl decyl dimethyl ammonium chloride, dioctyl dimethyl ammonium chloride, alkyl dimethyl benzyl ammonium chloride, and mixtures thereof. Nonionic surfactants may include, for example, ethoxylated and propoxylated alcohols, especially $C_{10-20}$ alcohols reacted with 2 to 100 moles of ethylene oxide and/or propylene oxide per mole of alcohol, especially ethoxylates of primary alcohols containing about 8 to 18 carbon atoms in a straight or branched chain configuration which have been reacted with about 5 to 30 moles of ethylene oxide, for example, the ethoxylates of decyl alcohol, cetyl alcohol, lauryl alcohol, or myristyl alcohol; ethoxylates of secondary aliphatic alcohols containing 8 to 18 carbon atoms in a straight or branched chain configuration with 5 to 30 moles of ethylene oxide; condensation of aliphatic alcohols containing about 8 to abut 20 carbon atoms with ethylene oxide and propylene oxide; polyethylene glycol and polyethylene oxide; ethoxylated castor oil; ethoxylated hydrogenated castor oil; ethoxylated coconut oil; ethoxylated lanolin; ethoxylated tall oil; ethoxylated tallow alcohol; and ethoxylates of sorbitan esters.

The disinfectant composition may comprise a thickening agent, which may be organic or inorganic. Inorganic thickening agents may include alkali metal silicates and very high surface area inorganic materials, such as finely divided silica or clays. Organic thickening agents may include cellulose ethers, such as methylcellulose; acrylic and methacrylic polymers and copolymers, such as copolymers of acrylic acid; and biopolymers, such as alginate. Polymer-based products, such as polyacrylic acid copolymers, may also be used. The concentration of the thickening agent, the nature of the thickening agent, and the nature and concentration of other materials present in the composition may influence the desired viscosity.

Other conventional ingredients may also be included, provided each ingredient is compatible with the other ingredients of the disinfectant composition and the presence of the ingredient does not adversely affect the properties of the disinfectant composition. Each additional ingredient may be used to modify the disinfectant composition in a conventional way and may be present in an effective amount, that is, in the amount required to achieve the desired effect without adversely affecting the properties of the composition. The disinfectant composition may include other bleaching agents, such as hydrogen peroxide releasing agents or hypochlorites. The disinfectant composition may comprise perfumes or fragrances, typically at about 0.03 wt % to about 1.0 wt % of the composition. Fluorescent whitening agents may also be present, typically at about 0.1 wt % to 1.0 wt %. An anti-redeposition agent, such as polyvinyl pyrrolidone, hydroxyethyl cellulose, sodium carboxymethyl cellulose, or hydroxypropyl ethyl cellulose, may be present. An electrolyte, such as sodium sulfate or sodium chloride, may be present. Other conventional ingredients include: preservatives; dyes and other colorants; UV absorbents or antioxidizing agents, fabric softening compositions; static control agents; optical opacifiers, such as polystyrene particles; and suds regulants, such as dimethylpolysiloxane.

After all of the other ingredients have been accounted for, water may comprise the balance of the disinfectant composition (i.e., the compositions may be aqueous disinfectant compositions). Depending on the application, it is often necessary to dilute the hydrogen peroxide with water to obtain the desired hydrogen peroxide concentration. The water may desirably be free from metal ions that would catalyze decomposition of hydrogen peroxide, such as ferrous ions, ferric ions, cupric ions, cuprous ions, manganous ions, and similar transition metal ions. The water may also be desirably free from organic material that would be oxidized by hydrogen peroxide. The water may also be desirably free of inorganic materials that would react with hydrogen peroxide, such as chlorine ($Cl_2$), hypochlorous acid (HOCl), and sodium hypochlorite (NaOCl). Distilled or deionized water is preferred.

In an exemplary embodiment, the disinfectant composition comprises 0.001 to 10% by weight of hydrogen peroxide or a peroxide source based on the total weight of the composition; 0.001 to 20% by weight of at least one amphoteric surfactant based on the total weight of the composition; and 0.001 to 0.8% by weight of at least one alkali metal or alkaline earth metal salt of a cyclic or heterocyclic aromatic compound comprising at least one hydroxyl group, carboxylic group, or a combination thereof; optional additives and conventional ingredients, such as stabilizers, etc.; and the balance is water.

The disinfectant composition may be used for any suitable purpose. For example, the composition may be used as a disinfectant, a sanitizer, and the like (e.g., as both a disinfectant and/or a bleaching agent). The particular use of the hydrogen peroxide composition is not especially limited. In one embodiment, the composition is used as a disinfectant or cleaning composition, which encompasses any composition that may be used for cleaning, such as industrial, commercial, and household cleaning, bleaching, and/or disinfectant solutions.

In one embodiment of the present invention, a method of making a disinfectant composition comprises mixing hydrogen peroxide or a precursor or source thereof, water, at least one amphoteric surfactant, and at least one alkali metal or alkaline earth metal salt of a cyclic or heterocyclic aromatic compound comprising at least one hydroxyl group, carboxylic group, or a combination thereof. The compositions may be prepared by adding the desired amount of each of the ingredients together. The ingredients may be added and mixed together using any suitable methods or techniques known in the art. For example, the ingredients may be added simultaneously or sequentially and may be mixed together to form a homogenous mixture. The pH may subsequently be adjusted to achieve the desired pH. As discussed above, the pH may be adjusted using any suitable pH adjuster. For example, the pH may be adjusted using an acid, such as sulfuric acid.

Before, during, or after the pH is adjusted, one or more additives may also be added and mixed into the composition. As discussed above, at least one additive may be selected from the group consisting of anionic surfactants, cationic surfactants, nonionic surfactants, bleaching agents, enzymes, fluorescent dyes, color dyes, fragrances, thickening agents, inorganic builders, anti-redeposition agents, corrosion inhibitors, opacifiers, and mixtures thereof.

The disinfectant compositions described herein have been found to provide good killing rates and killing power, especially for virulent bacterial strains, and produces effective wide spectrum biocidal activity. Thus, the disinfectant may be classified as "hospital strength" in that the compositions are effective on both Gram positive type and Gram negative type bacteria. For example, the disinfectant composition may be effective at attacking Gram negative bacteria, such as *Pseudomonas aeroginosa, Escherichia coli, Salmonella chloreaesuis*, as well as on Gram positive bacteria, such as *Enterococcus hirae, Staphylococcus aureus*, present on infected surfaces.

In an exemplary embodiment, the disinfectant compositions of the present invention having a high killing power (e.g., on the order of ≥99%, ≥99.9%, ≥99.99%, or ≥99.999%), which reduces or eliminates all or substantially all of the microorganisms (e.g., bacteria, fungi, spores, viruses, moulds and yeast, etc.) within 30 seconds or within 10 seconds. For example, the disinfectant composition may provide a killing rate of at least 99.999% for *Staphylococcus aureus* at 30 seconds.

The disinfectant composition may be packaged and used to treat a given surface in any suitable form known to one of ordinary skill in the art, such as liquid, spray, aerosol, foam, wipes, etc. For example, a liquid form of the disinfecting compositions may be packaged in manually operated spray dispensing containers (e.g., a trigger spray dispenser or in a pump spray dispenser). In such a dispenser, the liquid composition may be divided in fine liquid droplets resulting in a spray that is directed onto the surface to be treated (e.g., an atomized composition). The compositions may also be executed in the form of wipes (e.g., disposable towels incorporated/impregnated/wetted with the disinfecting composition therein).

According to one embodiment of the present invention, a method of disinfecting a surface contaminated with microorganisms comprises contacting the surface with the disinfectant compositions in accordance with the present invention. Surfaces may include hard-surfaces such as those typically found in hospital environments (e.g., operating theaters, surgical areas, recovery areas, moveable equipment such as gurneys, beds, and the like), medical laboratories, medical treatment environments, food services, food processing, and those found in residential and commercial spaces like kitchens, bathrooms, e.g., tiles, walls, floors, chrome, glass, smooth vinyl, any plastic, plastified wood, table top, sinks, cooker tops, dishes, sanitary fittings such as sinks, showers, shower curtains, wash basins, toilets, and the like. Moreover, a surface could include objects such as food objects (e.g., fruits and vegetables, food packaging), medical tools, food services equipment (e.g., utensils), and the like. Additionally, the surface could include a human or animal surface, such as skin (e.g., human skin) or hands. In an exemplary embodiment, the ingredient amounts (e.g., hydrogen peroxide concentration) should be selected so as to be non-irritating to skin.

EXAMPLES

Examples 1-7 were prepared by mixing composition containing hydrogen peroxide, amphoteric surfactant (i.e., AMPHOSOL® CA, a cocoamidopropyl betaine with 30% solids and 30% actives derived from a methyl ester, obtainable from Stepan Company, with offices in Northfield, Ill.), and/or sodium salicylate in the amounts shown in Table 1. The pH was adjusted by using NaOH and/or $H_2SO_4$ to the values shown in Table 1. Table 1 lists disinfectant compositions according to the invention and comparative examples (1-3), which shows the killing rates for *Staphylococcus aureus*.

at 10 minutes. Comparative Example 2 added AMPHOSOL® CA (cocoamidopropyl betaine). The amphoteric surfactant helped $H_2O_2$ to kill the germs faster at a time of 10 minutes, reaching 99.999% from 88.95% at 10 minutes, but it did not help at the time of 10 seconds or 30 seconds. Comparative Example 3 added sodium salicylate (without the amphoteric surfactant), which helped the $H_2O_2$ to kill the germs better than the amphoteric alone at the times of 10 seconds and 30 seconds, but produced worse results at the time of 10 minutes.

Example 4 showed that there is a great synergy for the germ killing when $H_2O_2$, amphoteric surfactant, and salicylate are used in combination. Example 5, which also provided >99.999% killing rate at 30 seconds, indicates that the synergy among the ingredients may also depend on the concentration of each ingredient. Examples 6 and 7 indicate that pH may also be an important factor (e.g., a more acidic pH of 3.5 worked much better than a pH of 6.0).

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A method of disinfecting a hard surface comprising:
    applying to a hard surface a disinfecting composition comprising (i) non-disinfecting components and (ii) a disinfecting combination consisting of 0.001 to 10% by weight of hydrogen peroxide or a hydrogen peroxide source based on the total weight of the composition; 0.001 to 20% by weight of at least one amphoteric surfactant based on the total weight of the composition; and 0.001 to 0.8% by weight of at least one alkali metal or alkaline earth metal salt of a cyclic or heterocyclic aromatic compound comprising at least one hydroxyl group, carboxylic group, or combination thereof based on the total weight of the composition wherein said disinfectant composition has a pH in the range of about 3-4, and wherein said disinfectant composition exhibits a kill rate for *staphylococcus aureus* of greater than 83% at 10 seconds.

2. The method according to claim 1, wherein the at least one amphoteric surfactant comprises a positive ion and a negative ion, wherein the positive ion and the negative ion are separated by more than one atom.

|  | $H_2O_2$ | AMPHOSOL Amphoteric Surfactant | Na Salicylate | pH | *S. aureus* killing rate** at | | |
|---|---|---|---|---|---|---|---|
|  |  |  |  |  | 10 seconds | 30 seconds | 10 minutes |
| Example 1 | 3% | — | — | 3.5 | 10.53% | 10.53% | 88.95% |
| Example 2 | 3% | 1% | — | 3.5 | 5.26% | 15.79% | >99.999% |
| Example 3 | 3% | — | 0.018% | 3.5 | 23.08% | 36.46% | 98.92% |
| Example 4 | 3% | 1% | 0.018% | 3.5 | 98.00% | 99.87% | >99.999% |
| Example 5 | 3% | 0.5% | 0.05% | 3.2 | 99.91% | >99.99% | >99.999% |
| Example 6 | 3% | 1% | 0.009% | 3.5 | 83.89% | 98.50% | >99.999% |
| Example 7 | 3% | 1% | 0.009% | 6.0 | 11.11% | 22.22% | 87.78% |

**all the killing rate data were the average from 2 replicates.

As shown in Table 1, comparative Example 1 shows $H_2O_2$ alone, which killed the *Staphylococcus aureus* slowly, reaching 10.53% killing rate at 10 seconds, and only 88.95%

3. The method according to claim 2, wherein the at least one amphoteric surfactant comprises nitrogen as the positive ion and oxygen as the negative ion.

4. The method according to claim 1, wherein the at least one amphoteric surfactant comprises a surfactant having the following formula:

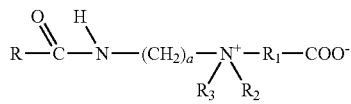

where R, $R_2$, and $R_3$ are each alkyl groups, $R_1$ is a saturated or unsaturated alkylene group, and $a \geq 1$.

5. The method according to claim 1, wherein the at least one amphoteric surfactant comprises an amidobetaine.

6. The method according to claim 5, wherein the at least one amphoteric surfactant comprises a cocamidopropyl betaine.

7. The method according to claim 1, wherein the at least one amphoteric surfactant is present at about 0.01 to 1% by weight based on the total weight of the composition.

8. The method according to claim 1, wherein the cyclic or heterocyclic aromatic compound is a salicylate.

9. The method according to claim 1, wherein the at least one alkali metal salt or alkaline earth metal is selected from the group consisting of sodium, potassium, magnesium, and calcium.

10. The method according to claim 1, wherein the at least one alkali metal or alkaline earth metal salt of the cyclic or heterocyclic aromatic compound is sodium salicylate.

11. The method according to claim 1, wherein the at least one alkali metal or alkaline earth metal salt of the cyclic or heterocyclic aromatic compound is present at about 0.04 to 0.06% by weight based on the total weight of the composition.

12. The method according to claim 1 wherein said non-disinfecting component comprises at least one pH adjusting agent.

13. The method according to claim 12, wherein the at least one pH adjusting agent is a base selected from the group consisting of alkali metal and alkaline earth metal hydroxides, ammonium hydroxide, substituted ammonium hydroxides, and mixtures thereof.

14. The method according to claim 12, wherein the at least one pH adjusting agent is an acid selected from the group consisting of sulfonic acids, sulfuric acid, alkali metal bisulfates, and mixtures thereof.

15. The method according to claim 1 wherein said non-disinfecting component comprises one or more additives selected from the group consisting of anionic surfactants, cationic surfactants, nonionic surfactants, bleaching agents, enzymes, fluorescent dyes, color dyes, fragrances, thickening agents, inorganic builders, anti-redeposition agents, corrosion inhibitors, opacifiers, and mixtures thereof.

16. The method according to claim 1, wherein the disinfectant composition is effective against gram positive bacteria.

17. The method according to claim 1, wherein the disinfectant composition provides a killing rate of at least 99.999% for *Staphylococcus aureus* at 30 seconds.

* * * * *